(12) United States Patent
Schmid et al.

(10) Patent No.: US 10,959,756 B2
(45) Date of Patent: Mar. 30, 2021

(54) TROCAR WITH REDUCED PROFILE (71) Applicant: Ethicon LLC, Guaynabo, PR (US)

(72) Inventors: Katherine J. Schmid, Loveland, OH (US); Jeffery Kirk, Liberty Township, OH (US)

(73) Assignee: Ethicon LLC, Guaynabo, PR (US)

( * ) Notice: Subject to any disclaimer, the term of this patent is extended or adjusted under 35 U.S.C. 154(b) by 471 days.

(21) Appl. No.: 15/380,483

(22) Filed: Dec. 15, 2016

(65) Prior Publication Data

US 2018/0168688 A1 Jun. 21, 2018

(51) Int. Cl.
*A61B 17/34* (2006.01)
*A61B 34/35* (2016.01)
(Continued)

(52) U.S. Cl.
CPC ...... *A61B 17/3474* (2013.01); *A61B 17/3462* (2013.01); *A61B 17/3498* (2013.01);
(Continued)

(58) Field of Classification Search
CPC . A61B 17/34; A61B 17/3462; A61B 17/3474; A61B 17/3498; A61B 5/150351; A61B 2017/3419; A61B 17/3415; A61M 13/003; A61M 39/10; A61M 13/006; A61M 39/06; A61M 2039/062; A61M 2039/0626; A61M 2039/0633; A61M 2039/229; A61M 25/0097; A61M 39/22; A61M 39/223; A61M 39/225; A61M 39/227; A61M 39/228; A61M 2039/224; A61M 2039/2473; A61M 2039/248; A61M 2039/2486
See application file for complete search history.

(56) References Cited

U.S. PATENT DOCUMENTS 3,017,050 A * 1/1962 Barr, Sr. .......... A61B 5/150213
215/247
4,730,624 A * 3/1988 Waters ............... A61B 5/15003
600/577
(Continued)

FOREIGN PATENT DOCUMENTS

WO WO-2012077366 A1 6/2012
WO 2014151621 A1 9/2014

OTHER PUBLICATIONS

International Search Report and Written Opinion for International App. No. PCT/IB2017/057297 dated Mar. 20, 2018 (14 pages).

*Primary Examiner* — William R Carpenter
*Assistant Examiner* — William R Frehe
(74) *Attorney, Agent, or Firm* — Mintz Levin Cohn Ferris Glovsky and Popeo, P.C.

(57) ABSTRACT

Methods and devices are provided for various insufflation sealing approaches for a trocar. For example, a trocar is provided that has a housing and a cannula extending therefrom. The housing and the cannula have a tool pathway extending therethrough for receiving a surgical tool, and the housing has an insufflation port therein. A variety of seal elements are provided that seal the insufflation port to prevent fluid flow into the port. The port and seal elements are configured to have a reduced profile to prevent interference between the trocar and a tissue surface during use.

11 Claims, 5 Drawing Sheets

(51) Int. Cl.
*A61M 13/00* (2006.01)
*A61M 39/10* (2006.01)
*A61M 39/24* (2006.01)
*A61B 34/00* (2016.01)
*A61M 39/22* (2006.01)

(52) U.S. Cl.
CPC .............. *A61B 34/35* (2016.02); *A61B 34/72* (2016.02); *A61M 13/003* (2013.01); *A61M 39/10* (2013.01); *A61M 39/24* (2013.01); *A61B 2017/3419* (2013.01); *A61M 2039/229* (2013.01); *A61M 2205/0216* (2013.01)

(56) References Cited

U.S. PATENT DOCUMENTS

| | | | |
|---|---|---|---|
| 4,857,062 A * | 8/1989 | Russell | A61M 39/0613 604/256 |
| 5,078,688 A * | 1/1992 | Lobodzinski | A61M 25/0606 604/167.05 |
| 5,545,150 A * | 8/1996 | Danks | A61B 17/3496 604/167.03 |
| 5,843,040 A | 12/1998 | Exline | |
| 6,123,689 A | 9/2000 | To et al. | |
| 7,568,394 B1 * | 8/2009 | Keilman | A61B 5/0215 361/283.4 |
| 8,114,345 B2 | 2/2012 | Dlugos, Jr. et al. | |
| 2005/0065454 A1 * | 3/2005 | Manoussakis | B01L 3/50825 600/576 |
| 2005/0070851 A1 | 3/2005 | Thompson et al. | |
| 2005/0288634 A1 * | 12/2005 | O'Heeron | A61B 17/3462 604/167.06 |
| 2010/0228096 A1 * | 9/2010 | Weisenburgh, II | A61B 17/3462 600/214 |
| 2011/0087169 A1 * | 4/2011 | Parihar | A61B 17/3474 604/167.03 |
| 2011/0172767 A1 * | 7/2011 | Rathi | A61B 17/0401 623/11.11 |
| 2012/0152238 A1 * | 6/2012 | Flickinger | A61M 15/08 128/200.21 |
| 2012/0238947 A1 * | 9/2012 | Ott | A61M 11/042 604/24 |
| 2013/0066281 A1 * | 3/2013 | Yavorsky | A61M 5/162 604/257 |
| 2015/0173792 A1 | 6/2015 | McGinley et al. | |
| 2017/0042573 A1 * | 2/2017 | Savvouras | A61B 1/05 |

* cited by examiner

TROCAR WITH REDUCED PROFILE

FIELD

Trocars having a reduced profile, and methods for using such a trocar, are provided.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

Trocars are provided having various insufflation port configurations. In one embodiment, a trocar assembly is provided and includes a trocar having a housing and a cannula extending distally from the housing. The housing and the cannula have a tool pathway extending therethrough for receiving a tool. At least one seal is disposed within the housing and extending across the pathway, the at least one seal being configured to form at least one of a seal across the pathway when no tool is disposed therethrough and a seal around a tool when a tool is inserted therethrough to thereby seal an insufflation fluid within the housing. The trocar further includes a port formed in a sidewall of the housing at a location distal of the at least one seal. The port is in fluid communication with the tool pathway.

In one embodiment, the trocar includes a stopcock assembly removably matable to the port for allowing the delivery of insufflation fluid to the tool pathway, and a plug removably matable to the port for sealing the port when the stopcock assembly is removed from the port. In certain aspects, the port can include a female luer connector formed therein and configured to receive a male luer connector formed on the stopcock assembly. The stopcock assembly can include a valve for selectively opening and closing a fluid flow path extending through the stopcock assembly.

The plug can have a variety of configurations, but in one embodiment the plug is elastomeric. The plug can be configured to be held within the port by a friction fit.

In other aspects, the port can be fully disposed without the housing and does not project outward from a sidewall of the housing.

In another embodiment, a trocar assembly is provided and includes a trocar having a housing and a cannula extending distally from the housing. The housing and the cannula have a tool pathway extending therethrough for receiving a tool. At least one seal is disposed within the housing and extends across the pathway. The at least one seal is configured to form at least one of a seal across the pathway when no tool is disposed therethrough and a seal around a tool when a tool is inserted therethrough to thereby seal an insufflation fluid within the housing. The trocar also includes a port formed in a sidewall of the housing at a location distal of the at least one seal. The port is in fluid communication with the tool pathway.

In one embodiment, a flapper door extends across the port and is movable between a closed position, in which the flapper door forms a seal across the port, and an open position in which the flapper door is configured to mate to an insufflation tubing assembly for the delivery of insufflation fluid into the tool pathway. In certain aspects, the flapper door can be biased to the closed position, and is configured to automatically move to an open position when an insufflation tubing assembly is coupled thereto.

The port can have various configurations, and can include a female luer connector for receiving a male luer connector on an insufflation tubing assembly. The port can be fully disposed without the housing and does not project outward from a sidewall of the housing.

The trocar can also include an insufflation tubing assembly having a mating element formed on an end thereof and configured to be received within the port for mating the insufflation tubing to the port.

In another embodiment, a trocar assembly is provided and includes a trocar having a housing and a cannula extending distally from the housing. The housing and the cannula have a tool pathway extending therethrough for receiving a tool.

At least one seal is disposed within the housing and extends across the pathway. The at least one seal is configured to form at least one of a seal across the pathway when no tool is disposed therethrough and a seal around a tool when a tool is inserted therethrough to thereby seal an insufflation fluid within the housing. A port is formed in a sidewall of the housing at a location distal of the at least one seal. The port is in fluid communication with the tool pathway.

In an exemplary embodiment, a one-time seal extends across the port to seal the port. The one-time seal is configured to be punctured when an insufflation tubing is mated to the port. The one-time seal can be, for example, a film In certain aspects, the port is fully disposed without the housing and does not project outward from a sidewall of the housing. The port can include a female luer fitting formed therein and configured to receive a male luer fitting formed on an insufflation tubing. In a further embodiment, the trocar can include an insufflation tubing assembly having a mating element formed on an end thereof and configured to be received within the port for mating the insufflation tubing to the port.

Methods for using the above devices are also disclosed herein.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various surgical tools and methods are provided that are configured to prevent interference between an insufflation port and a tissue surface during use of a trocar. Trocars generally have a housing and a cannula extending from the housing with a tool pathway extending through the housing and the cannula to receive a surgical tool. A seal is formed across the tool pathway, and the housing is able to connect to an insufflation pathway, for example through insufflation tubing, to deliver insufflation through the trocar and cannula and into a body cavity of a patient. A typical trocar has a stopcock assembly formed on and projecting from a sidewall of the housing for mating to an insufflation tube. One problem with current trocars is that the stopcock assembly has a high profile which can increase a risk that the stopcock assembly will interfere with use of the device. This is especially the case in robotic surgery, wherein multiple tools extending through multiple trocars are manipulated simultaneously. The stopcock assembly on each trocar has been known to "crash" into the tissue surface or other trocars and tool. While the stopcock assembly can be oriented during setup to avoid such collisions, this can undesirably add additional time to the procedure. Trocars having a low profile and alternative configurations for coupling to an insufflation tubing are thus provided.

Figure 1:
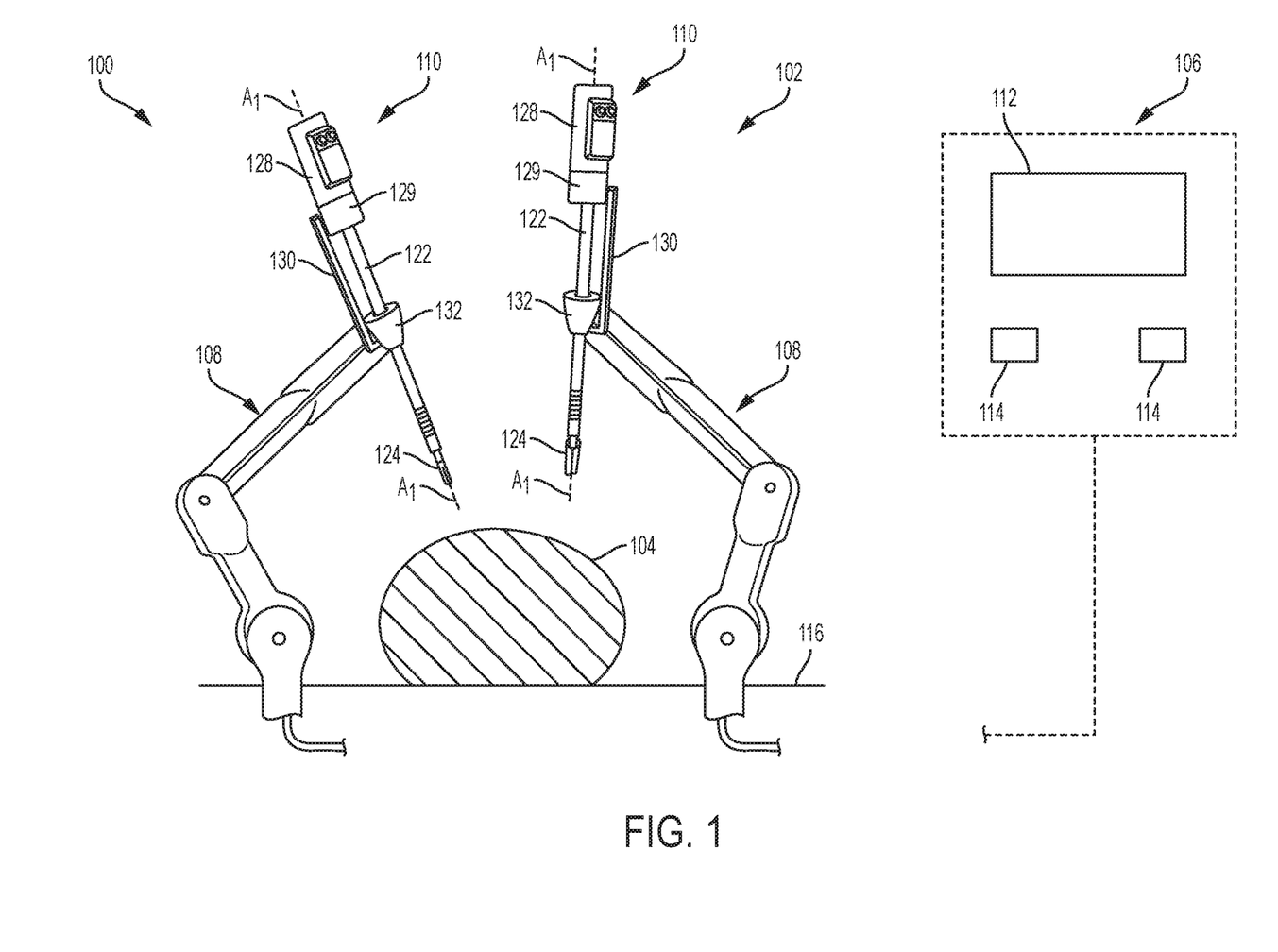
FIG. 1 is a perspective view of one embodiment of a surgical robotic system that includes a patient-side portion and a user-side portion.

FIG. 1 is a perspective view of one embodiment of a surgical robotic system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more surgical tools and/or tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each surgical tool 110 during a surgical procedure. A person skilled in the art will appreciate that the surgical robotic system can have a variety of configurations. One exemplary system is disclosed in WIPO Patent Publication No. WO2014/151621, filed on Mar. 13, 2014 and entitled "Hyperdexterous Surgical System," which is incorporated herein by reference in its entirety.

The patient-side portion 102 can have a variety of configurations. As illustrated in FIG. 1A the patient-side portion 102 is coupled to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 1A). Alternatively, the patient-side portion 102 can include a single assembly that includes one or more robotic arms 108 extending therefrom.

The surgical tool 110 includes an elongate shaft 122, an end effector 124, and a tool housing 128 coupled to a proximal end of the shaft 122. The shaft 122 can have any of a variety of configurations. In general, the shaft 122 is an elongate member extending distally from the housing 128 and having at least one inner lumen extending therethrough. The shaft 122 is fixed to the housing 128, but in other embodiment the shaft 122 can be releasably coupled to the housing 128 such that the shaft 122 can be interchangeable with other shafts. This may allow a single housing 128 to be adaptable to various shafts having different end effectors. The end effector 124 can also have a variety of sizes, shapes, and configurations. The end effector 124 can be configured to move relative to the shaft 122, e.g., by rotating and/or articulating, to position the end effector 124 at a desired location relative to a surgical site during use of the tool 110. The housing 128 includes various components (e.g., gears and/or actuators) configured to control the operation various features associated with the end effector 124 (e.g., any one or more of clamping, firing, rotation, articulation, energy delivery, etc.). In at least some embodiments, as in this illustrated embodiment, the surgical tool 110 is configured to releasably couple to a tool driver 129 mounted on a carrier 130 on the distal end of the robotic arm 108. The tool housing 128 can include coupling features configured to allow the releasable coupling of the tool 110 to the tool driver 129. The carrier 130 can also include a trocar or a trocar support 132 mounted on a distal end thereof and configured to receive a shaft 122 of the tool 110 therethrough. A person skilled in the art will appreciate that the surgical tool 110 can have any of a variety of configurations, and it can be configured to perform at least one surgical function. The surgical tool can be, for example, a stapler, a clip applier, forceps, a grasper, a needle driver, scissors, an electrocautery tool that applies energy, a suction tool, an irrigation tool, an imaging device (e.g., an endoscope or ultrasonic probe), etc.

The control system 114 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exo-skeletal glove, a powered and gravity-compensated manipulator, or the like. The one or more input devices can control teleoperated motors which, in turn, control the movement of the surgical system, including the robotic arms 108 and surgical tools 110.

As indicated above, in an exemplary embodiment the trocar has a low profile to prevent collisions during use with other tools and/or the tissue surface. In general, the trocar includes a housing and a cannula extending distally therefrom. A tool pathway extends through the housing and the cannula for receiving an elongate shaft of a surgical tool, such as the shaft 122 of surgical tool 110, to allow an end effector on the tool to be positioned within a body cavity.

In order to facilitate viewing within the body cavity and manipulation of the end effector, the trocar can be configured to allow an insufflation fluid to be passed therethrough and into a body cavity to inflate the body cavity. In order to present escape of the insufflation fluid through the proximal opening in the trocar, the trocar can include any numbers of seals disposed therein and configured to form a seal across the tool pathway when no tool is present and/or when a tool is disposed through the pathway. By way of example, a trocar can include a first seal that seals across the channel when no instrument is present. The first seal can be, for example, a channel seal such as zero-closure seal or flapper valve. The trocar can also include a second seal, such as an instrument seal, that forms a seal around a shaft of a tool passed through the tool pathway. The second seal can be, for example, a duckbill seal, a multilayer seal, etc.

In order to allow delivery of an insufflation fluid into the housing of the trocar, the housing can further include an insufflation port formed therein. In an exemplary embodiment, the insufflation port is configured so as to have a low profile and to allow for rapid connection and disconnected of an insufflation tubing assembly.

Figure 2A:
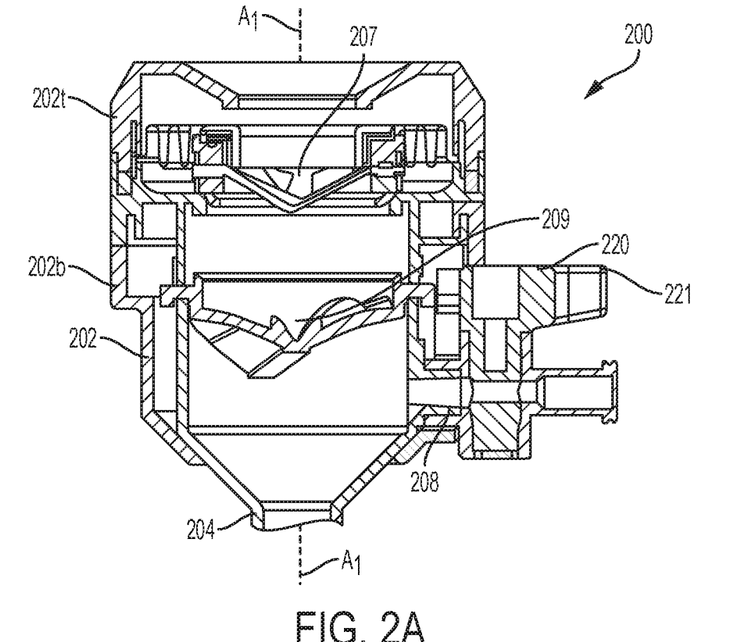
FIG. 2A is a cross-sectional view of one embodiment of a trocar with a removable stopcock assembly.

FIG. 2A illustrates one embodiment of a trocar 200 with a housing 202 and a cannula 204 extending distally from the housing. A tool pathway extends through an opening 206 in the housing 202 and through the cannula 204 along a longitudinal axis A1. The housing 202 has a top portion 202t and a bottom portion 202b with a first seal, e.g., an instrument seal 207, extending therebetween to provide a seal across the tool pathway. A second seal, such as a channel seal 209, is disposed within the housing distal of the instrument seal 207, and the channel seal 209 forms a seal across the channel with no tool is inserted through the trocar.

Figure 2B:
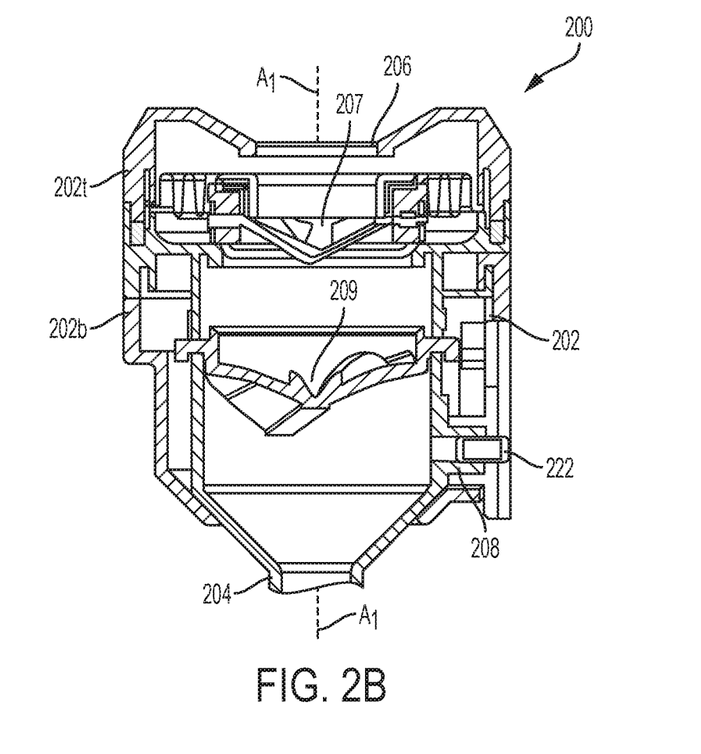
FIG. 2B is a cross-sectional view of the trocar of FIG. 2A with a removable plug.

As further shown in FIG. 2A, an insufflation port 208 is formed within a sidewall of the housing 202 such that it is fully-contained within and does not project from the housing 202. The port 208 is in the form of an opening extending through the sidewall and in fluid communication with the tool pathway. In this embodiment, the trocar includes a stopcock 220 that can be removably mated to the port 208. Insufflation tubing can be connected to the stopcock 220 for delivering an insufflation fluid through the port 208 and into the tool pathway for delivering into a body cavity of a patient during use. If the stopcock 220 is not needed, the stopcock 220 can be removed and a plug 222 can be inserted into the port 208, as illustrated in FIG. 2B. The plug 222 can seal the port 208 and allow the trocar 200 to operate as usual. If insufflation is needed during use, a user can remove the plug 222 and attach the removable stopcock 220 as desired. If insufflation is not needed, for example if multiple trocars are in use and another trocar is providing insufflation, the user can insert the plug 222. The removable stopcock 220 and the plug 222 provide the freedom to choose between a low profile configuration during use of the plug 222, and selectively using the stopcock 220 with insufflation as needed.

The stopcock 220 can be mated to the port 208 using a variety of techniques. In the illustrated embodiment, the port 208 is tapered and thus forms a female luer fitting. The stopcock 220 has a corresponding male luer formed thereon that is received within the port for mating the stopcock 220 to the port. The stopcock 220 can, however, be attached to the port 208 in a variety of ways, such as by press-fit, a mechanical connection, a clasp or other locking feature, etc. The plug 222 can also mate to the port 208 using a variety of techniques. In the illustrated embodiment, the plug is elastomeric and thus compresses when it is inserted into the port to form a seal while also maintaining the plug therein by friction fit. The plug 222 can have a tapered configuration as well, as shown in FIG. 2B, to facilitate mating a formation of a secure seal. The plug can be entirely disposed within the port 208 to be unobtrusive or it can partially extend from the port 208 radially outward to allow easier manipulation and removal. The plug can take a variety of forms and be made of a variety of materials. For example, the plug can be square, rectangular, cylindrical, etc., and the plug can be made from an elastomer or other sealing material.

The stopcock 220 can have a variety of configurations, but in generally should have a fluid pathway formed therethrough and configured to communicate with the port 208 for allowing the delivery of insufflation fluid into the trocar. The stopcock 220 can optionally include a lever 221 coupled thereto for opening and closing the insufflation pathway extending through the stopcock 220.

Figure 3A:
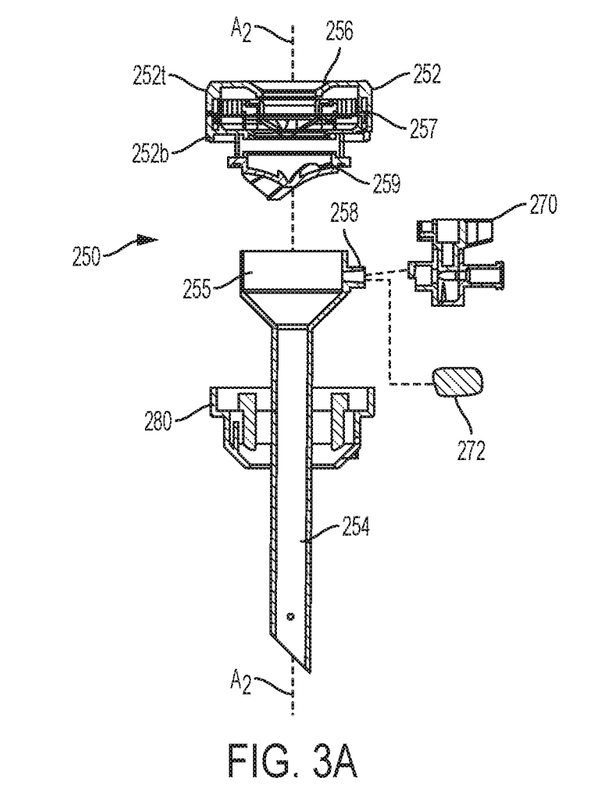
FIG. 3A is a cross-sectional, exploded view of another embodiment of a trocar with a removable stopcock assembly.
Figure 3B:
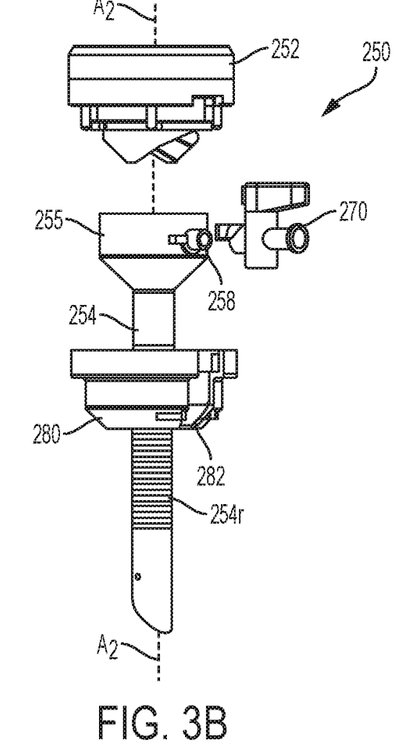
FIG. 3B is a perspective, exploded view of the trocar of FIG. 3A.

FIGS. 3A-3B illustrate another embodiment of a trocar 250 with an outer housing 252 and a cannula 254 extending distally from the housing. The outer housing 252 and the cannula 254 are modular and are capable of being coupled and uncoupled from one another. The cannula 254 is in the form of a hollow elongate tube having a plurality of ribs 254r formed along an outer surface thereof and an inner housing 255 at its proximal end. The outer housing includes a top portion 252t and a bottom portion 252b that seat and engage the inner housing 255 therebetween. A tool pathway extends through an opening 256 in the outer housing 252 and through the cannula 254 along a longitudinal axis A2. A first seal, e.g., an instrument seal 257, is disposed within the top portion 252t of the outer housing 252 and forms a seal across the tool pathway. A second seal, such as a channel seal 259, is disposed within the top portion 252t of the outer housing distal of the instrument seal 257, and forms a seal across the channel when no tool is inserted through the trocar.

An insufflation port 258 is formed within a sidewall of the inner housing 255. The port 258 is in the form of an opening extending through the sidewall and in fluid communication with the tool pathway. The trocar 250 can include a stopcock assembly 270 that can be removably mated to the port 258. Insufflation tubing can be connected to the stopcock assembly 270 for delivering an insufflation fluid through the port 258 and into the tool pathway and into a body cavity of a patient during use. If the stopcock assembly 270 is not needed, the stopcock assembly 270 can be removed and a plug 272 can be inserted into the port 258. The plug 272 can seal the port 258 and allow the trocar 250 to operate as usual. If insufflation is needed during use, a user can remove the plug 272 and attach the removable stopcock assembly 270 as desired. If insufflation is not needed, for example if multiple trocars are in use and another trocar is providing insufflation, the user can insert the plug 272. The removable stopcock assembly 270 and the plug 272 provide the freedom to choose between a low profile configuration during use of the plug 272, and selectively using the stopcock 270 with insufflation as needed. A trocar support 280 can be used to support and hold the trocar 250, and the trocar support 280 can have a cut-out 282 that receives the port 258 and the stopcock 270 or the plug 272.

Figure 4:
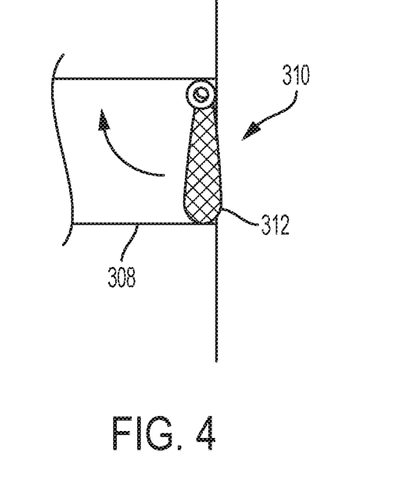
FIG. 4 is a cross-sectional view of a portion of a trocar having a port with a spring-loaded flapper valve shown in a closed configuration.
Figure 5:
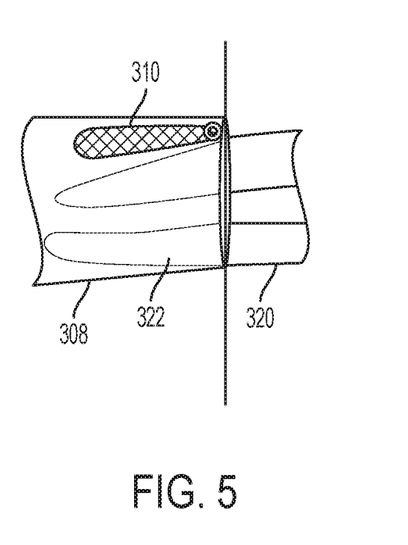
FIG. 5 is a cross-sectional view of the trocar of FIG. 4 with the spring-loaded flapper valve in an open configuration and having an insufflation tubing inserted therein.
Figure 6:
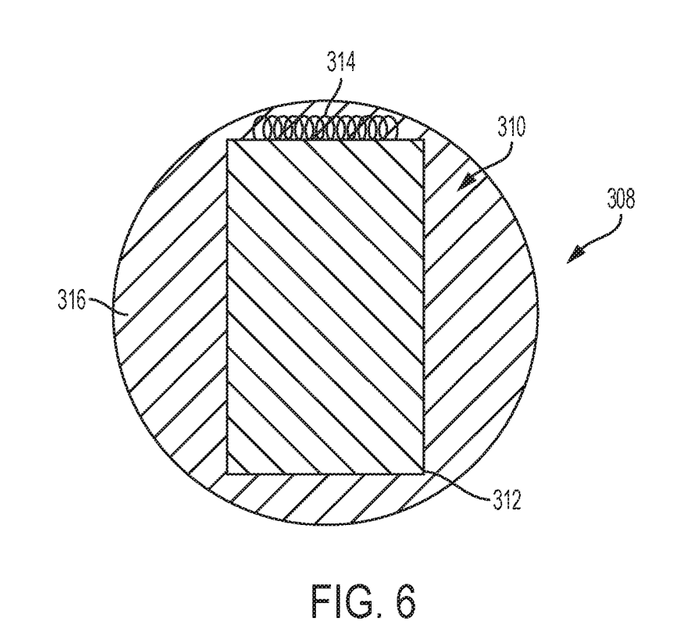
FIG. 6 is a front view of the trocar port of FIG. 4 with the spring-loaded flapper valve closed.

FIGS. 4-6 illustrate a portion of another embodiment of a trocar housing having an insufflation port 308 formed therein. While the port 308 is shown fully disposed within a sidewall of the housing such that it does not project from the housing, the port 308 in other embodiments can project from the housing by a certain distance. The trocar and the port can have a configuration similar to that described above with respect to FIGS. 2 and 3. In this embodiment, the port 308 has a spring-loaded flapper valve 310 that closes over and seals the port 308. The valve 310 can be biased to the closed configuration, shown in FIG. 4, to seal the port 308 when not in use. The flapper valve 310 generally includes a solid door 312, such as a piece of rigid plastic, that is on a spring-loaded hinge 314. The spring-loaded hinge 314 biases the door 312 closed. In one embodiment, an outer perimeter of the door 312 can be surrounded by an elastomeric seal 316 that, combined with the door 312 in its closed position, seals the port 308. The elastomeric seal 316 can be made from a flexible material, such as an elastomeric material, to allow movement of the seal.

During use, a stopcock (such as stopcock 220) or an insufflation tube 320 can be inserted into the port 308, causing the door 312 to move to an open configuration thereby allowing the tube 320 to mate to the port 308, as illustrated in FIG. 5. In an exemplary embodiment, the door 312 moves into the port 308 as it transitions from the closed position to the open position so as to allow the door 312 to move in response to insertion of the insufflation tubing or stopcock therein. The elastomeric seal 316 will seal around the tube 320, and the tube 320 can provide insufflation through the port 308. Insertion of the tube 320 into the port 308 will thus automatically connect the insufflation pathway. When the tube 320 is removed, the spring bias can cause the door to return to the closed position, thereby automatically disconnecting the insufflation pathway and sealing the port 308.

Various techniques can be used to coupling an insufflation tube to the port 308, including those described above with respect to FIGS. 2 and 3. In the illustrated embodiment, the insufflation tube 320 has a male mating member 322 on a distal end that is configured and shaped to push the door 312 open. The male mating member 322 is press-fit into the port 308. A variety of other mating configurations can be used. For example, the insufflation tube and the insufflation port can use a luer twist connection, press-fit, a male and female mating mechanism, etc. A stopcock lever and/or valve can be disposed on the insufflation tubing 320, which would provide a user a way to open and close the insufflation pathway created by connecting the tubing 320 and the port 308, but a lever and/or valve is not required. Insufflation ports can be embedded, recessed, and/or fully contained within a trocar to reduce a profile of the trocar or can extend therefrom to allow easier access and use of the port.

Figure 7:
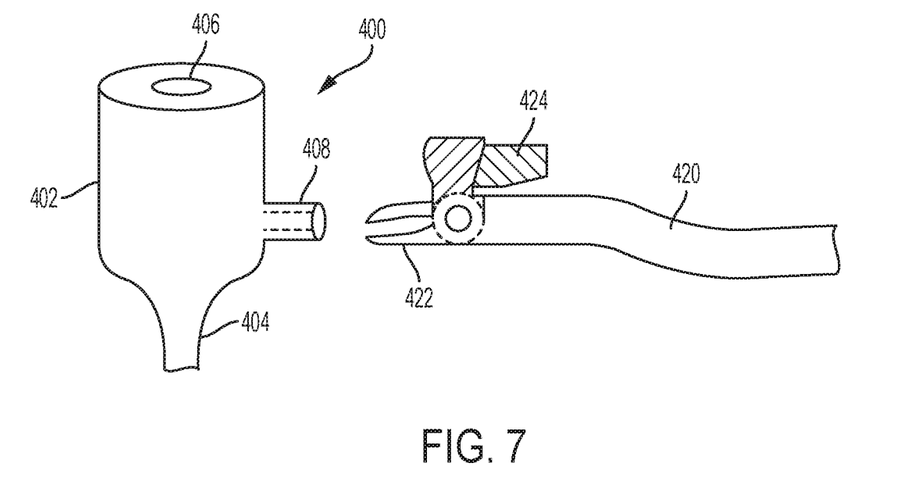
FIG. 7 is a perspective view of a trocar with a port having a one-time seal and showing an insufflation tube about to be passed into the port.
Figure 8:
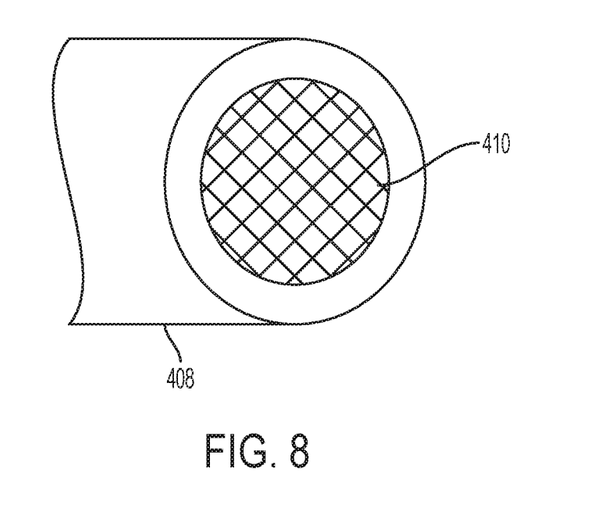
FIG. 8 is a perspective view of the port and one-time seal of FIG. 7.

FIGS. 7 and 8 illustrate another embodiment of a trocar having a housing 402 and a cannula 404 extending distally therefrom. The housing has insufflation port 408 projecting from the sidewall thereof, however the port 408 can be fully recessed and contained within the sidewall similar to ports 208, 308. A tool pathway extends through an opening 406 in the housing 402 and through the cannula 404, and at least one seal is disposed within the housing 402 to provide a seal across the tool pathway. The insufflation port 408 has a sealing film 410 (represented by cross-hatching in FIG. 8) that extends across an opening in the port 408 to seal the port 408. The sealing film can be made from a variety of materials and can take a variety of forms, such as a cellophane membrane, a gel, an elastomeric plug, a cap, etc. The sealing film 410 is preferably configured for one-time use, such that it is incapable of forming a seal after an insufflation tubing is mated to the port.

During use, an insufflation tube 420 can be inserted into the port 408, piercing the sealing film 410 that extends across the port 408, thus allowing entry of the tube 420 into the port 408. The tube 420 forms a seal with the port 408 and provides an insufflation pathway through the trocar 400. The illustrated insufflation tube 420 has a male mating member 422 on a distal end that is configured and shaped to pierce the sealing film 410. The male mating member 422 can be press-fit within the port 408 to create a seal. A variety of different mating connections can be used, such as a male and female luers or other male and female mating mechanism, clasps or latches, press-fit, friction fit, etc.

As indicated above, the sealing film 410 is a one-time use film, which cannot be resealed once the tube 420 is inserted into the port 408 and the male mating member 422 pierces the film 410. However, other embodiments can have a sealing film, such as a gel membrane, that could re-seal and re-open as the insufflation tube was detached and re-attached as needed.

A stopcock lever 424 can be disposed on the insufflation tube 420, which allows a user to selectively open and close the insufflation pathway created by connecting the tube 420 and the port 408. A variety of opening and closing valves, levers, etc., can be used, but a stopcock and/or lever and/or valve is not required.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

The systems, devices, and methods disclosed herein can be implemented using one or more computer systems, which may also be referred to herein as digital data processing systems and programmable systems.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A trocar assembly, comprising:
   a trocar having a housing and a cannula extending distally from the housing, the housing and the cannula having a tool pathway extending therethrough for receiving a tool;
   at least one seal disposed within the housing and extending across the tool pathway, the at least one seal being configured to form at least one of a first sealing engagement across the tool pathway when no tool is disposed therethrough and a second sealing engagement around the tool when the tool is inserted therethrough to thereby seal an insufflation fluid within the housing; and
   a port formed in a sidewall of the housing at a location distal of the at least one seal, the port being in fluid communication with the tool pathway, the port being fully disposed within the housing such that the port does not project outward from the sidewall of the housing;
   a stopcock assembly removably matable to the port for allowing the delivery of the insufflation fluid to the tool pathway; and
   a removable plug having an outer surface perpendicular to an axis of the port, the outer surface facing away from an interior of the port, the outer surface being configured to be entirely disposed within the port, and the plug being configured to seal the port when the stopcock assembly is removed from the port.

2. The trocar assembly of claim 1, wherein the port includes a female luer connector formed therein and configured to receive a male luer connector formed on the stopcock assembly.

3. The trocar assembly of claim 1, wherein the stopcock assembly includes a valve for selectively opening and closing a fluid flow path extending through the stopcock assembly.

4. The trocar assembly of claim 1, wherein the plug is elastomeric.

5. The trocar assembly of claim 1, wherein the plug is configured to be held within the port by a friction fit.

6. A trocar assembly, comprising:
   a trocar having a housing and a cannula extending distally from the housing, the housing and the cannula having a tool pathway extending therethrough for receiving a tool;
   at least one seal disposed within the housing and extending across the tool pathway, the at least one seal being configured to form at least one of a first sealing engagement across the tool pathway when no tool is disposed therethrough and a second sealing engagement around the tool when the tool is inserted therethrough to thereby seal an insufflation fluid within the housing;

a port formed in a sidewall of the housing at a location distal of the at least one seal, the port being in fluid communication with the tool pathway; and a removable plug having an outer surface perpendicular to an axis of the port, the outer surface facing away from an interior of the port, the outer surface being configured to be entirely disposed within the port, and the plug being configured to seal the port when an insufflation tubing is not mated to the port.

7. The trocar assembly of claim 6, wherein the port is fully disposed within the housing and does not project outward from the sidewall of the housing.

8. The trocar assembly of claim 6, wherein the port includes a female luer fitting formed therein and configured to receive a male luer fitting formed on the insufflation tubing.

9. The trocar assembly of claim 6, further comprising an insufflation tubing assembly having a mating element formed on an end thereof and configured to be received within the port for mating the insufflation tubing to the port.

10. The trocar assembly of claim 6, further comprising a one-time seal extending across the port to seal the port prior to use, the one-time seal being configured to be punctured when the insufflation tubing is initially mated to the port.

11. The trocar assembly of claim 10, wherein the one-time seal comprises a film.

* * * * *